US00PP28594P3

(12) United States Plant Patent
Yoshiie

(10) Patent No.: US PP28,594 P3
(45) Date of Patent: Nov. 7, 2017

(54) APPLE TREE NAMED 'KIRAMEKI'

(50) Latin Name: *Malus domestica*
Varietal Denomination: Kirameki

(71) Applicant: Kazuo Yoshiie, Nagano (JP)

(72) Inventor: Kazuo Yoshiie, Nagano (JP)

( * ) Notice: Subject to any disclaimer, the term of this patent is extended or adjusted under 35 U.S.C. 154(b) by 0 days.

(21) Appl. No.: 14/998,618

(22) Filed: Jan. 21, 2016

(65) Prior Publication Data

US 2016/0219766 P1 Jul. 28, 2016

Related U.S. Application Data

(60) Provisional application No. 62/107,180, filed on Jan. 23, 2015.

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Annette Para
(74) *Attorney, Agent, or Firm* — Lathrop & Gage LLP

(57) ABSTRACT

A new and distinct apple variety is described, the variety results from controlled cross pollination between ((Jonathan×Pink Pearl)×Fuji). This variety can be characterized by its full golden coloration sometimes with a light blush with very limited over color and intense red fleshed appearance. The new variety has been named 'Kirameki'.

2 Drawing Sheets

Genus and species plant claimed: *Malus domestica.*
Variety denomination: 'Kirameki'.

BACKGROUND OF THE INVENTION

The present invention relates to a new and distinct variety of *Malus domestica* hereinafter referred to by the cultivar name 'Kirameki'. The new plant variety described herein resulted from controlled cross pollination between (Jonathan×Pink Pearl)×Orin performed in 2005 in Nagano prefecture, Japan. The controlled cross was performed in the inventor's apple orchard. Approximately 15 hybrid seeds were sown in the spring of 2006, and top grafting on 16 year-old Fuji trees ('CG24' rootstock) was performed using their scions in spring of 2007 in Nagano. The year of first bearing was 2010 and the variety was selected in 2001. The new variety was determined to be distinct from the parent varieties.

SUMMARY OF THE INVENTION

This variety can be characterized by its full golden coloration sometimes with a light blush with very limited over color and intense red fleshed appearance. The variety is also different in that the harvest time is similar to that of Fuji and flowers early. The new variety has been named 'Kirameki'. 'Kirameki' was asexually reproduced and is currently grown in Japan under Japanese conditions.

'Kirameki' was determined to be distinct from the parent varieties 'Irodori' (Jonathan×Pink Pearl) and 'Orin', as well as the closely related variety, 'Moon rouge', by the following characteristics. 'Kirameki' has yellow colored fruit skin compared with Irodori which has red colored fruit skin. 'Kirameki' has red colored fresh compared with 'Orin' which does not. 'Kirameki' has ovoid fruit shape compared with 'Moon rounge' which is conic. Fresh firmness of 'Kirameki' is harder than 'Moon rouge'. 'Kirameki' has more acidity than 'Moon rouge' 'Kirameki' has a later harvest (early/mid November) than 'Pink Pearl' (mid September)

BRIEF DESCRIPTION OF THE DRAWINGS

The accompanying colour photographs show typical specimens of the tree, foliage and fruit of the new variety as depicted in colours as nearly true as is reasonably possible to make the same in a colour illustration of this character.

DETAILED DESCRIPTION

Figure 1:
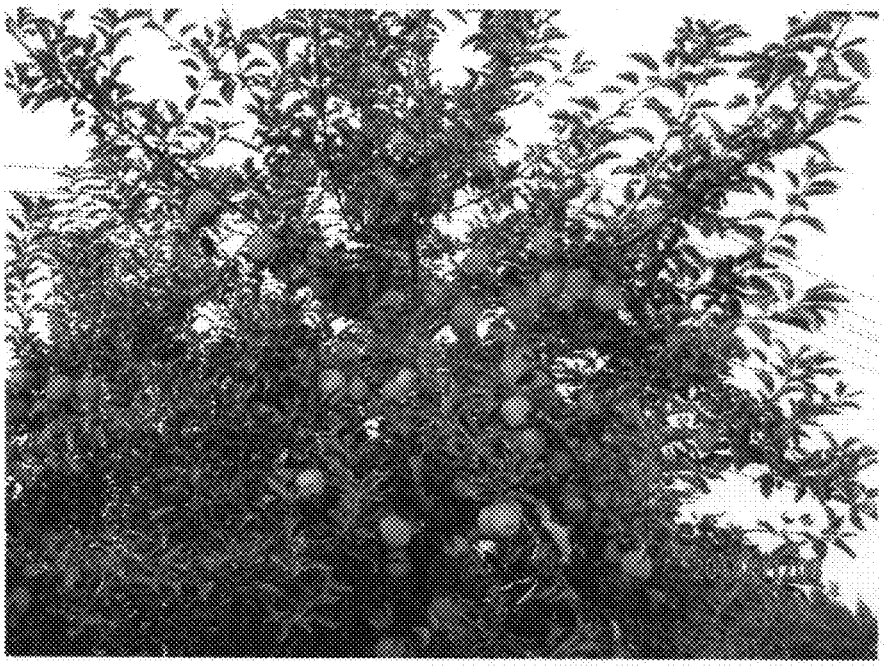
FIG. 1 shows fruit and foliage on the tree
Figure 2:
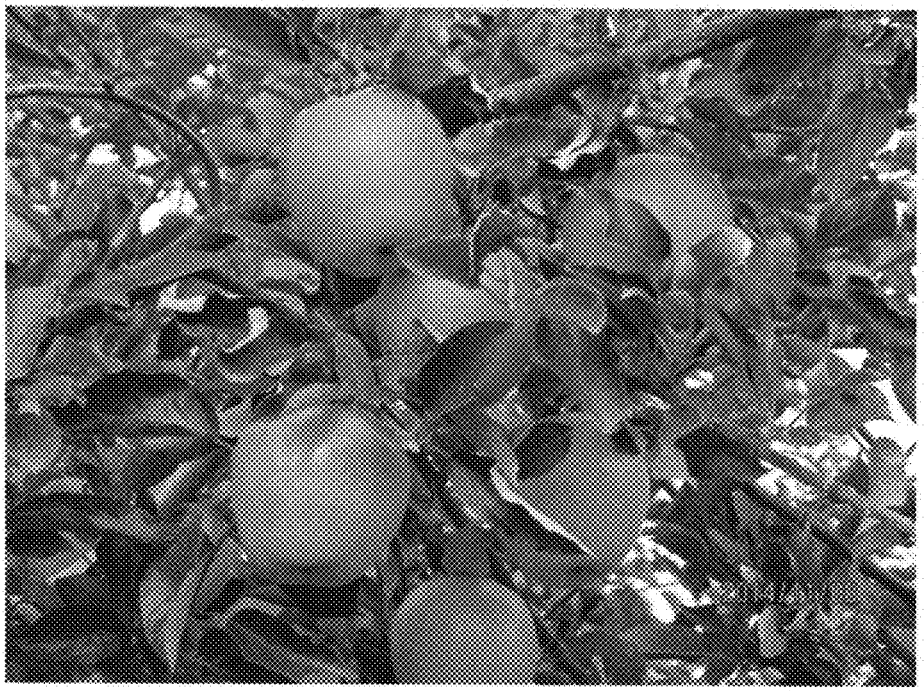
FIG. 2 shows a close up view of fruit and foliage on the tree
Figure 3:
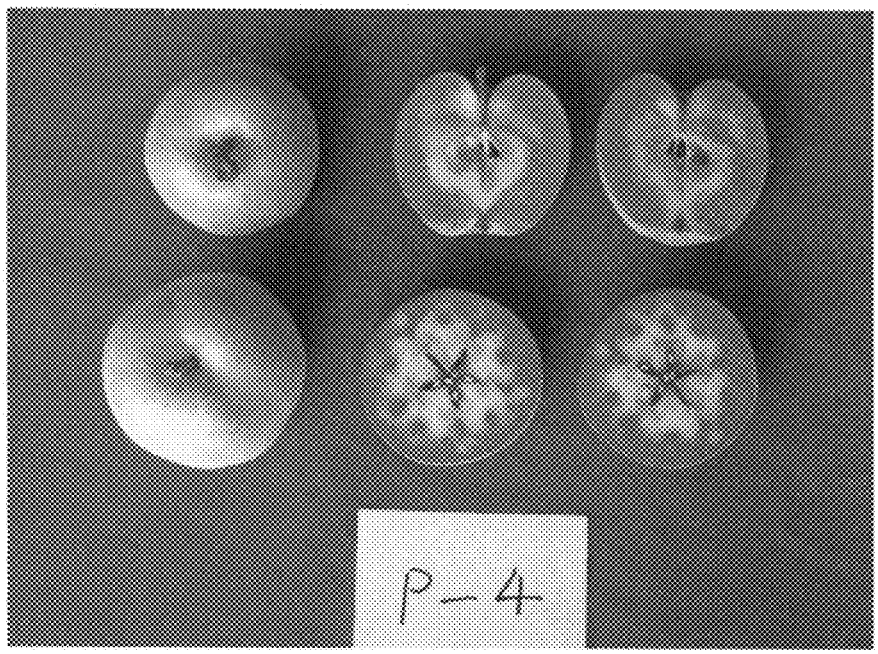
FIG. 3 shows uncut fruit and transverse sections through fruit.
Figure 4:
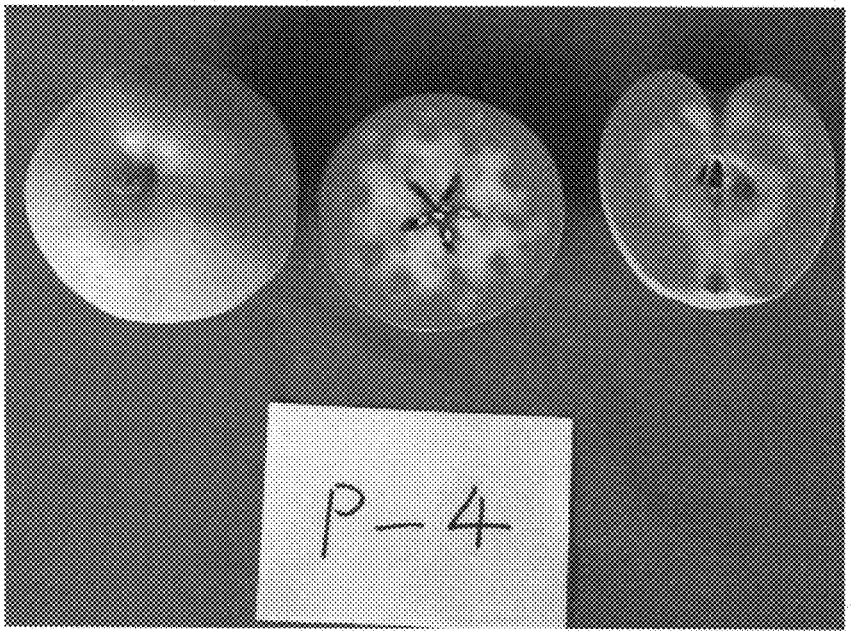
FIG. 4 shows a close up view of uncut fruit, and transverse and longitudinal sections through fruit.

The following botanical description is based on observations made during the 2013 growing season in Nagano prefecture, Japan. The observations are based on top grafted (8 year-old) branches on 16 year-old 'Fuji'/CG24. Color observations are made in accordance with the Japan Horticultural Standard Color Chart (JHSCC). The following is a detailed description of the new variety:

Plant description:

*Breeding*.—Produced by controlled pollination.
*Parents*.—(Jonathan×Pink Pearl)×Orin.
*Method of propagating the variety*.—Vegetative propagation through grafting.
*Tree type*.—Ramified.
*Tree habit*.—Upright.
*Trunk* (*bark*).—Dull yellow-green — 3110 (JHSCC).
*Branches*.—Dull yellow green, 3110 (JHSCC).
*Height* (5 *year old tree*).—4.0 m.
*Trunk diameter* (*at* 30 *cm about the graft*).—8.4 cm.

Foliage description:

*Length of internode* (*one-year-old shoot*).—Short (2.6 cm).

*Number of lenticels* (*one-year-old shoot*).—Medium.

*Lenticel shape*.—Round.

*Lenticel number/cm*$^2$.—13.6.

*Lenticel color*.—Light gray, 02 (JHSCC).

*Color* (*one year-old shoot*).—Deep reddish brown, 1013 (JHSCC).

*Leaf blade attitude in relation to shoot*.—Upwards.

*Leaf blade length*.—Medium (10.8 cm).

*Leaf blade width*.—Medium (5.6 cm).

*Leaf blade ratio length/width*.—Medium (1.93).

*Leaf color*.—Deep yellow green, 4006 (JHSCC).

*Petiole length*.—Medium (2.7 cm).

Flower description:

*Predominant color at balloon stage*.—Vivid purplish red, 9707 (JHSCC).

*Diameter with petals pressed into horizontal position*.—Small (3.5 cm).

*Arrangement of petals*.—Free.

*Time of beginning of flowering* (10% *open flowers*).—Early.

Fruit:

*Fruit size*.—Large (300 g). Weight (300 g under Japanese cultivating technique).

*Height*.—Tall (8.7 cm).

*Diameter*.—Large (8.6 cm).

*Ratio height/diameter*.—Large (1.01).

*Size of eye*.—Small.

*Bloom of skin*.—Absent or weak.

*Area of russet around stalk attachment*.—Absent or small.

*Area of russet around eye basin*.—Absent or small.

*Fruit skin color*.—Bright yellow, 2506 (JHSCC).

*Length of stalk*.—Medium (2.1 cm).

*Thickness of stalk*.—Medium (2.3 mm).

*Depth of stalk cavity*.—Deep (1.7 cm).

*Width of stalk cavity*.—Medium (4.0 cm).

*Depth of eye basin*.—Shallow (0.3 cm).

*Width of eye basin*.—Medium (1.7 cm).

*Aperture of locules* (*in transverse section*).—Moderately open.

*General shape of fruit*.—Obloid.

*Relative area of over colour of fruit*.—Absent or very small (Granny Smith).

*Observed dates for harvest period*.—Early/mid November, Nagano prefecture, Japan.

*Time of eating maturity*.—Late (Fuji).

*Color of flesh* (*red color part*).—Deep red 0408 (JHSCC). Acidity of flesh is low.

*Titlate acidity*.—1.20%.

*Soluble solids*.—14.2%.

*Firmness*.—20.3 lb.

*Duration of storage*.—Common and cold storage is very long.

*Cold storage*.—Two months.

*Shelf life*.—Two weeks.

*Disease susceptibility*.—No known resistances to pests and diseases.

I claim:

1. A new and distinct apple tree substantially as illustrated and described herein.

* * * * *